United States Patent [19]

Endoh et al.

[11] Patent Number: 5,434,268
[45] Date of Patent: Jul. 18, 1995

[54] PROCESS FOR THE MANUFACTURE OF TRIAZOLECARBOXAMIDE

[75] Inventors: Kiichi Endoh; Masanori Itoh; Takeo Watanabe; Takafumi Shida, all of Fukushima, Japan

[73] Assignee: Kureha Chemical Industry Co., Ltd.

[21] Appl. No.: 221,688

[22] Filed: Mar. 31, 1994

[30] Foreign Application Priority Data

Mar. 31, 1993 [JP] Japan ................... 5-096603

[51] Int. Cl.⁶ .............................. C07D 249/08
[52] U.S. Cl. ..................................... 548/266.8
[58] Field of Search ................... 548/266.8

[56] References Cited

FOREIGN PATENT DOCUMENTS 070089 5/1982 European Pat. Off. .
0282303 10/1988 European Pat. Off. .

OTHER PUBLICATIONS

Journal of the American Chemical Society vol. 79, No. 8, 1957, Rearrangement of 4-arylazo-2-phenyloxazolin-5-ones.
Journal of the Chemical Society 1962, London GM, Triazoles. Part IV.

*Primary Examiner*—Patricia L. Morris
*Attorney, Agent, or Firm*—Burgess, Ryan & Wayne

[57] ABSTRACT

A process for the manufacture of 1-(substituted or unsubstituted)phenyl-5-(substituted or unsubstituted)-phenyl-1H-1,2,4-triazole-3-carboxamide of the formula (I), which comprises heating 2-(substituted or unsubstituted)phenyl-4,5-oxazoledione 4-(substituted or unsubstituted)phenylhydrazone of the formula (II) and ammonia in water according to the following reaction formula,

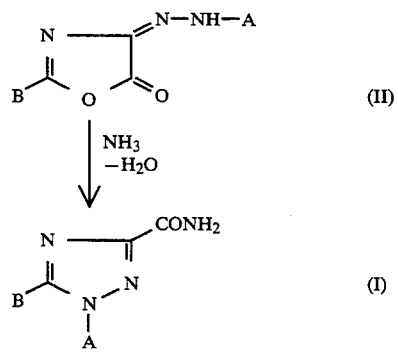

wherein A and B individually represent one or more substituted or unsubstituted phenyl groups. The target compound can be manufactured at a high purity and a high yield without using an organic solvent or an acidic compound.

5 Claims, No Drawings

PROCESS FOR THE MANUFACTURE OF TRIAZOLECARBOXAMIDE

BACKGROUND OF THE INVENTION

1. Field of the Invention

The present invention relates to a process for the manufacture of 1-(substituted or unsubstituted)phenyl-5-(substituted or unsubstituted)phenyl-1H-1,2,4-triazole-3-carboxamide which is useful as an effective component of agriculture chemical compositions.

2. Description of Background Art

The following two methods are known for manufacturing 1-(substituted or unsubstituted)phenyl-5-(substituted or unsubstituted)phenyl-1-1,2,4-triazole-3-carboxamide (hereinafter referred to as triazolecarboxamide).

(1) A method of heating 2-(substituted or unsubstituted)phenyl-4,5-oxazoledione 4-(substituted or unsubstituted)phenylhydrazone (hereinafter referred to as a hydrazone derivative) in an aqueous methanol containing a large excess of ammonia.

(2) A method comprising heating a hydrazone derivative in an organic solvent, such as acetone, dioxane, or toluene, containing excess ammonia, and cyclocondensing the product with hydrochloric acid or acetic acid.

These methods, however, have still to be improved with respect to the use of organic solvents as a dispersing medium or as a solvent, the use of acidic compounds as a cyclocondensation catalyst, and the like.

The present inventors have undertaken extensive studies in order to develop a more simple and economical process for the manufacture of triazolecarboxamides, and found triazolecarboxamides can be produced without using organic solvents or acidic compounds, but only using water as a dispersion medium or as a solvent.

SUMMARY OF THE INVENTION

Accordingly, an object of the present invention is to provide a novel process for manufacturing a triazolecarboxamide using only water as a dispersion medium or as a solvent, and without using organic solvents or acidic compounds.

The present invention relates to a process for manufacturing a triazolecarboxamide comprising heating a hydrazone derivative and ammonia in water.

A more specific object of the present invention is to provide a process for the manufacture of 1-(substituted or unsubstituted)phenyl-5-(substituted or unsubstituted)phenyl-1H-1,2,4-triazole-3-carboxamide of the formula (I), which comprises heating 2-(substituted or unsubstituted)phenyl-4,5-oxazoledione 4-(substituted or unsubstituted)phenylhydrazone of the formula (II) and ammonia in water according to the following reaction formula,

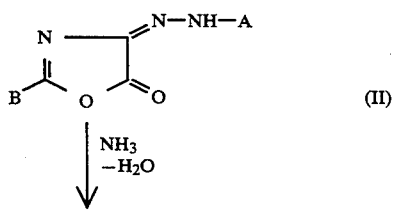

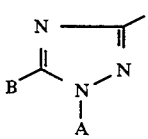

wherein A and B individually represent a substituted or unsubstituted phenyl group.

Other objects, features and advantages of the invention will hereinafter become more readily apparent from the following description.

DETAILED DESCRIPTION OF THE INVENTION AND PREFERRED EMBODIMENTS

The hydrazone derivative of formula (II) is first ring-opened by the reaction with ammonia, and then cyclocondensed to produce the triazolecarboxamide of formula (I).

The process of the present invention can be applied to any hydrazone derivatives having substitution groups on two types of benzene rings (phenyl groups) which are present in the raw material hydrazone, but which do not react when heated with ammonia in water.

The phenyl group represented by B in formula (II) may be either unsubstituted or substituted by up to five substitution groups. The following groups are given as examples of the substitution groups. When two or more groups are substituted, these substituted groups may be either the same or different.

Halogen atoms, $C_1$–$C_6$ alkyl groups, $C_1$–$C_6$ alkoxy groups, $C_1$–$C_6$ fluoroalkyl groups, $C_1$–$C_4$ fluoroalkoxy groups, nitro group, HO group, and $R^3OCH_2$ groups, wherein $R^3$ represents a $C_1$–$C_6$ alkyl group or a $C_1$–$C_6$ fluoroalkyl group, witch a preferred group being a $C_2$–$C_5$ fluoroalkyl group.

Throughout the present specification, the subscripted numbers for C indicate the number of carbon atoms.

The phenyl group represented by A in formula (II) may be either unsubstituted or substituted by up to five substitution groups. The following groups are given as examples of the substitution groups. When two or more groups are substituted, these substituted groups may be either the same or different.

Halogen atoms, $C_1$–$C_6$ alkyl groups, $C_1$–$C_6$ alkoxy groups, $C_1$–$C_6$ alkylthio groups, $C_1$–$C_6$ (preferably $C_1$–$C_4$) fluoroalkyl groups, cyano group, nitro group, and $R^2OCH(R^1)$ groups, wherein $R^1$ represents a hydrogen atom, a $C_1$–$C_6$ alkyl group, a $C_3$–$C_6$ cycloalkyl group, a $C_1$–$C_6$ (preferably $C_1$–$C_5$) fluoroalkyl group, a phenyl group, a $C_1$–$C_4$ alkyl-, $C_1$–$C_4$ alkoxy-, or a halogen-substituted phenyl group; and $R^2$ represents a hydrogen atom, a $C_1$–$C_8$ alkyl group, a ($C_3$–$C_6$ cycloalkyl)($C_1$–$C_4$ alkyl) group (preferably a ($C_3$–$C_6$ cycloalkyl)methyl group), a $C_3$–$C_6$ cycloalkyl group, a $C_1$–$C_6$ (preferably $C_2$–$C_5$) fluoroalkyl group, a $C_3$–$C_6$ alkenyl group, a $C_3$–$C_6$ alkynyl group, a phenyl group, a $C_1$–$C_4$ alkyl, $C_1$–$C_4$ alkoxy, $C_1$–$C_4$fluoroalkyl, or a halogen-substituted phenyl group, a phenyl($C_1$–$C_4$ alkyl) group (preferably phenylmethyl group), a $C_1$–$C_4$ alkyl-, $C_1$–$C_4$ alkoxy-, or halogen-substituted phenyl($C_1$–$C_4$ alkyl) group (preferably a $C_1$–$C_4$ alkyl-, $C_1$–$C_4$ alkoxy-, or halogen-substituted phenylmethyl group), a ($C_1$–$C_4$ alkoxy)($C_1$–$C_4$ alkyl) group, a ($C_3$–$C_4$ alkenyloxy)($C_1$–$C_4$ alkyl) group, a phenoxy($C_1$–$C_4$ alkyl) group (preferably a phenoxyethyl group), or a $C_1$–$C_4$ alkyl- or halogen-substituted phenoxy($C_1$–$C_4$ alkyl) group (preferably a $C_1$–$C_4$ alkyl- or halogen-substituted phenoxyethyl group).

In the above definitions, a halogen atom means fluorine, chlorine, bromine, or iodine atoms; and fluoroalkyl or fluoroalkoxy groups indicate alkyl or alkoxy groups with one or more hydrogen atoms being substituted by fluorine atoms.

Compounds listed in Table 1 are given as examples of hydrazone derivatives which are the raw materials in the present invention.

In Table 1, the substituted groups for the (substituted or unsubstituted)phenyl groups representing A or B in formula (II) are described according to the following rules.

The phenyl groups with no substituted groups are designated as "Unsubstituted". For phenyl groups having substituted groups, the substituted groups are designated by (position of the substituted group)-(type of the substituted group). For indicating the position of the substituted group, the ortho was indicated by 2 or 6, meta by 3 or 5, and para by 4. "Ph" stands for phenyl group and "i-" stands for "iso-". Accordingly, a methyl group bonded to the meta-position is described as "3-$CH_3$".

TABLE 1

| (Substituted or unsubstituted) phenyl group representing A in formula (II) | (Substituted or unsubstituted) phenyl group representing B in formula (II) |
|---|---|
| Unsubstituted | Unsubstituted |
| 3-$CH_3$ | Unsubstituted |
| 4-$C_2H_5$ | Unsubstituted |
| 3-$CH_3OCH_2$ | Unsubstituted |
| 3-n-$C_4H_9OCH_2$ | 2-F |
| 4-Cl | |
| 3-$CF_3$ | Unsubstituted |
| 4-Cl | |
| 3-(cyclopropylmethoxy)methyl | Unsubstituted |
| 3-(cyclohexylmethoxy)methyl | Unsubstituted |
| 3-neo-$C_5H_{11}OCH_2$ | 2-F |
| 3-n-$C_3F_7CH_2OCH_2$ | 4-$CH_3$ |
| 3-n-$C_3F_7CH_2OCH_2$ | 4-Cl |
| 3-n-$C_3F_7CH_2OCH_2$ | 4-$CH_3O$ |
| 3-$C_2F_5CH_2OCH_2$ | Unsubstituted |
| 4-$C_2H_5$ | |
| 3-$C_2F_5CH_2OCH_2$ | Unsubstituted |
| 4-Cl | |
| 3-$C_2F_5CH_2OCH_2$ | 2-F |
| 4-Cl | |
| 3-$C_2F_5CH_2OCH_2$ | Unsubstituted |
| 4-Cl | |
| 6-Cl | |
| 3-$C_2F_5CH_2OCH_2$ | Unsubstituted |
| 3-n-$C_5H_{11}OCH_2$ | Unsubstituted |
| 3-iso-$C_5H_{11}OCH_2$ | Unsubstituted |
| 4-Cl | |
| 6-Cl | |
| 3-iso-$C_5H_{11}OCH_2$ | 4-$CH_3O$ |
| 3-$CH_2$=$CHCH_2OCH_2$ | 2-F |
| 3-$PhCH_2OCH_2$ | Unsubstituted |
| 3-(p-$CH_3$Ph)$CH_2OCH_2$ | Unsubstituted |
| 3-(m-ClPh)$CH_2OCH_2$ | Unsubstituted |
| 3-$HOCH_2$ | Unsubstituted |
| 3-(p-$CF_3$Ph)$OCH_2$ | Unsubstituted |
| 3-(p-$CH_3$Ph)$OCH_2$ | Unsubstituted |
| 3-(p-ClPh)$OCH_2$ | 2-F |
| 3-$C_6F_5OCH_2$ | Unsubstituted |
| 3-(p-$CH_3$OPh)$OCH_2$ | Unsubstituted |
| 3-$CH_3$ | 4-Br |
| 4-$CH_3$ | |
| 3-$CH_3$ | 4-$NO_2$ |
| 4-$CH_3$ | |
| 3-$CH_3$ | 4-$NO_2$ |
| 3-$CH_3$ | Unsubstituted |
| 3-CN | Unsubstituted |
| 3-Cl | Unsubstituted |
| 4-Cl | |
| 2-F | 3-$CHF_2CF_2CH_2OCH_2$ |
| Unsubstituted | 3-n-$C_3F_7CH_2OCH_2$ |
| Unsubstituted | 3-$CH_3$ |
| Unsubstituted | 3-Cl |
| Unsubstituted | 3-Cl |
| | 4-Cl |
| Unsubstituted | 4-$NO_2$ |
| Unsubstituted | 4-$CH_3O$ |
| 2-$CH_3O$ | Unsubstituted |
| 5-Cl | |
| 4-$CH_3O$ | Unsubstituted |
| 3-$CH_3S$ | Unsubstituted |
| 3-[(n-$C_4H_9O$)CH(cyclopropyl)] | Unsubstituted |
| 3-[(n-$C_4H_9O$)CH(cyclopentyl)] | Unsubstituted |
| 3-[(n-$C_4H_9O$)CH(t-$C_4H_9$)] | 2-F |
| 3-[(Ph$CH_2O$)CH(t-$C_4H_9$)] | Unsubstituted |
| 3-[(n-$C_4H_9O$)CH(n-$C_3F_7$)] | Unsubstituted |
| 6-$CH_3$ | |
| 3-[(n-$C_4H_9O$)CH(n-$C_3H_7$)] | Unsubstituted |
| 3-[(n-$C_4H_9O$)CH($C_2H_5$)] | 2-F |
| 6-$CH_3$ | 3-F |
| 3-[(n-$C_4H_9O$)CH(i-$C_4H_9$)] | Unsubstituted |
| 3-[(n-$C_4H_9O$)CH($CH_3$)] | 2-F |
| 6-Cl | 3-F |
| | 5-F |
| | 6-F |
| 3-[(n-$C_4H_9O$)CH($CH_3$)] | Unsubstituted |
| 6-$CH_3O$ | |
| 3-[(n-$C_4H_9O$)CH($CH_3$)] | Unsubstituted |
| 6-$CH_3$ | |
| 3-(cyclohexylmethoxy)CH(i-$C_3H_7$) | 3-$CH_3$ |
| 3-[(n-$C_4H_9O$)CH(i-$C_3H_7$)] | 2-Cl |
| | 6-F |
| 3-[(n-$C_4H_9C$)CH(i-$C_3H_7$)] | 2-F |
| 6-$CH_3$ | |
| 3-[(n-$C_4H_9O$)CH(i-$C_3H_7$)] | 2-F |
| 6-$CH_3$ | 3-F |
| 3-[(n-$C_4H_9O$)CH(i-$C_3H_7$)] | 2-F |
| 6-$CH_3$ | 5-F |
| 3-[(n-$C_4H_9O$)CH(i-$C_3H_7$)] | 2-$CH_3$ |
| 6-$CH_3$ | |
| 3-[(n-$C_4H_9O$)CH(i-$C_3H_7$)] | 2-i-$C_3H_7$ |
| 6-$CH_3$ | |
| 3-[(n-$C_4H_9O$)CH(i-$C_3H_7$)] | 2-$CF_3O$ |
| 3-[($C_2H_5CC_2H_4O$)CH(i-$C_3H_7$)] | Unsubstituted |
| 3-[(ph$CH_2O$)CH(i-$C_3H_7$)] | Unsubstituted |
| 3-[(ph$CH_2O$)CH(i-$C_3H_7$)] | 2-OH |
| 3-[((2-$CH_3$Ph)$CH_2O$)CH(i-$C_3H_7$)] | Unsubstituted |
| 3-[((4-ClPh)$CH_2O$)CH(i-$C_3H_7$)] | Unsubstituted |
| 3-[(PhO)CH(i-$C_3H_7$)] | Unsubstituted |
| 3-[(n-$C_4H_9O$)CH(Ph)] | Unsubstituted |
| 4-$NO_2$ | Unsubstituted |
| 3-(n-$C_4H_9OCH_2CH_2O$)$CH_2$ | Unsubstituted |
| 3-($CH_2$=$CHCH_2OCH_2CH_2O$)$CH_2$ | Unsubstituted |
| 3-(Ph$CH_2OCH_2CH_2O$)$CH_2$ | Unsubstituted |
| 3-(PhO$CH_2CH_2O$)$CH_2$ | Unsubstituted |
| 3-((m-$CH_3$Ph)O$CH_2CH_2O$)$CH_2$ | Unsubstituted |
| 3-((p-ClPh)O$CH_2CH_2O$)$CH_2$ | Unsubstituted |

The hydrazone derivatives used in the present invention can be prepared by the methods disclosed in U.S. Pat. Ser. No. 4,973,353, EP-A-310555, or EP-A-493124. The method described in EP-A-493124 is particularly preferred.

Specifically, a substituted or unsubstituted aniline is diazotized to produce a salt of substituted or unsubstituted benzene diazonium, which is mixed with substituted or unsubstituted hippuric acid, acetic anhydride, and a neutralization agent, and stirred to obtain a hydrazone derivative. In this instance, as described in EP-A-493124, there is no need for the mixture of the substituted or unsubstituted hippuric acid and acetic anhydride to be heated in advance and cooled before these are reacted with the salt of substituted or unsubstituted benzene diazonium. In addition, there are no restrictions as to the manner in which the neutralization agent is added. The substituted groups for the aniline and hippuric acid are respectively those for 4-(substituted)-phenyl hydrazone and 2-(substituted)phenyl group in the hydrazone derivative.

The amount of ammonia used in the present invention is 1.2 to 15 mols, preferably 1.5 to 8 mols, and more preferably 2 to 5 mols, for 1 mol of the hydrazone derivative.

The amount of water, including water charged to the reaction system, water contained in the ammonia aqueous solution, and water contained in the hydrazone derivative, is 80 to 220 mols, preferably 100 to 200 mols, and more preferably 120 to 180 mols, for 1 mol of the hydrazone derivative.

The use of ammonia or water in amounts greater than 15 mol or 220 mol, respectively, only requires a large reaction vessel and a complicated reaction procedure, resulting in poor economy. The production of the triazolecarboxamides by the use of such amounts of ammonia or water is, of course, possible and included in the scope of the present invention.

The mixture of the hydrazone derivative, ammonia, and water is heated at 45°–150° C., preferably 65°–85° C., for 0.5–12 hours, preferably 1.5–6 hours, while stirring, whereupon the reaction mixture is cooled, and the solid is collected by filtration and dried to obtain high purity triazolecarboxamide at a high yield.

The reaction temperature higher than 100° C. under pressure or the reaction time longer than 12 hours may be employed without a reduction in the purity or the yield, if the hydrolysis of carboxamide into carboxylic acid can be avoided by taking sufficient precautions to the conversion rate of the hydrazone derivative to triazolecarboxamides.

As clear from the foregoing descriptions, because the process of the present invention does not require the use of organic solvents or acidic compounds, it is possible to prepare a high purity 1-(substituted or unsubstituted)-phenyl-5-(substituted or unsubstituted) phenyl-1H-1,2,4-triazole-3-carboxamide at a high yield using simple equipment by a easy procedure as compared with conventional processes in which the use of an organic solvent or an acidic compound is indispensable.

Other features of the invention will become apparent in the course of the following description of the exemplary embodiments which are given for illustration of the invention and are not intended to be limiting thereof.

EXAMPLES

Example 1

Preparation of 1-[4-chloro-3-(2,2,3,3,3-pentafluoropropoxymethyl)-phenyl]-5-phenyl-1-H-1,2,4-triazole-3-carboxamide A 29% ammonia aqueous solution (8.82 g, 150 mmol) was added to 100 g of water, and to the solution was added 2-phenyl-4,5-oxazoledione 4-[4-chloro-3-(2,2,3,3,3-pentafluoropropoxy)methylphenyl]hydrazone (39.7 g, purity: 97%, water content: 40%, 50 mmol). The mixture was vigorously stirred to produce a slurry. The slurry was heated to 80° C. in a water bath. In the course of the heating, the slurry abruptly changed its color, exhibiting an increase in the viscosity, at 65°–70° C.

The completion of the reaction was confirmed after stirring for two hours at 80° C., whereupon the reaction mixture was cooled and filtered. The residue was washed with water to obtain 34.3 g of a cake, which was dried at 60° C. to obtain 23.4 g of a dry powder of the target compound.

mp: 138°–140° C. Purity: 96.5% Yield: 98.0% NMR (CDCl$_3$, δ, ppm, 60 MHz) 3.78 (2H, tq, 13Hz, 2Hz) 4.73 (2H, s) 6.6–7.8 (10H, m)

Wherein "s" represents singlet, "t" a triplet, "q" quartet, and "m" multipier.

Example 2

Preparation of 1-[4-chloro-3-(2,2,3,3,3-pentafluoropropoxymethyl)-phenyl]-5-phenyl-1H-1,2,4-triazole-3-carboxamide A 29% ammonia aqueous solution (3.48 kg, 59.2 mol) was added to 47.8 kg of water. 2-phenyl-4,5-oxazoledione 4-[4-chloro-3-(2,2,3,3,3-pentafluoropropoxy)methylphenyl]hydrazone (14.9 kg, purity: 94.4%, water content: 36.5%, 19.4 mol) was added to the solution and the mixture was heated while stirring. After heating at 80° C. for two hours (after three hours after initiation of the heating), the reaction mixture was cooled to 50° C. and filtered by centrifugation. The residue was washed with hot water dried in a hot air drier to obtain 9.0 kg of the target compound.

Purity: 96.7% Yield: 98.3%

Obviously, numerous modifications and variations of the present invention are possible in light of the above teachings. It is therefore to be understood that within the scope of the appended claims, the invention may be practiced otherwise than as specifically described herein.

What is claimed is:

1. A process for the manufacture of 1-(substituted or unsubstituted)phenyl-5-(substituted or unsubstituted)-phenyl-1H-1,2,4-triazole-3-carboxamide of the formula (I), which comprises heating 2-(substituted or unsubstituted)phenyl-4,5-oxazoledione 4-(substituted or unsubstituted)phenylhydrazone of the formula (II) and ammonia in water according to the following reaction formula,

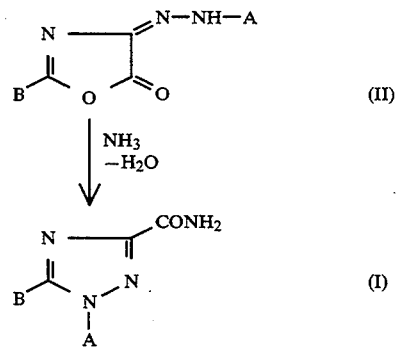

wherein A and B individually represent one or more substituted or unsubstituted phenyl groups.

2. The process according to claim 1, wherein the amount of ammonia used is 1.2 to 15 mols for 1 mol of the hydrazone derivative.

3. The process according to claim 1, wherein mixture of the hydrazone derivative, ammonia, and water is heated at 45°–150° C. for 0.5–12 hours while stirring.

4. The process according to claim 1, wherein the substituted phenyl groups represented by B in formula (II) has 1 to 5 substituted groups selected from the group consisting of fluoro, chloro, bromo, iodo groups, $C_1$-$C_6$ alkyl groups, $C_1$-$C_6$ alkoxy groups, $C_1$-$C_6$ fluoroalkyl groups, $C_1$-$C_4$ fluoroalkoxy groups, nitro group, HO group, and $R^3OCH_2$ groups, wherein $R^3$ represents a $C_1$-$C_6$ alkyl group or a $C_1$-$C_6$ fluoroalkyl group, and fluoroalkyl or fluoroalkoxy groups indicate alkyl or alkoxy groups with one or more hydrogen atoms being substituted by fluorine atoms, and further wherein when two or more substituted groups are present, these substituted groups may be either the same or different.

5. The process according to claim 1, wherein the substituted phenyl groups represented by A in formula (II) has 1 to 5 substituted groups selected from the group consisting of halogen atoms, $C_1$-$C_6$ alkyl groups, $C_1$-$C_6$ alkoxy groups, $C_1$-$C_6$ alkylthio groups, $C_1$-$C_6$ fluoroalkyl groups, cyano group, nitro group, and $R^2OCH(R^1)$ groups (wherein $R^1$ represents a hydrogen atom, a $C_1$-$C_6$ alkyl group, a $C_3$-$C_6$ cycloalkyl group, a $C_1$-$C_6$ fluoroalkyl group, a phenyl group, a $C_1$-$C_4$ alkyl-, $C_1$-$C_4$ alkoxy-, or a halogen-substituted phenyl group; and $R^2$ represents a hydrogen atom, a $C_1$-$C_8$ alkyl group, a ($C_3$-$C_6$ cycloalkyl)($C_1$-$C_4$ alkyl) group, a $C_3$-$C_6$ cycloalkyl group, a $C_1$-$C_6$ fluoroalkyl group, a $C_3$-$C_6$ alkenyl group, a $C_3$-$C_6$ alkynyl group, a phenyl group, a $C_1$-$C_4$ alkyl, $C_1$-$C_4$ alkoxy, $C_1$-$C_4$ fluoroalkyl, or a halogen-substituted phenyl group, a phenyl($C_1$-$C_4$ alkyl) group, a $C_1$-$C_4$ alkyl-, $C_1$-$C_4$ alkoxy-, or halogen-substituted phenyl($C_1$-$C_4$ alkyl) group, a ($C_1$-$C_4$ alkoxy)($C_1$-$C_4$ alkyl) group a ($C_3$-$C_4$ alkenyloxy)($C_1$-$C_4$ alkyl) group, a phenoxy($C_1$-$C_4$ alkyl) group, and a $C_1$-$C_4$ alkyl- or halogen-substituted phenoxy($C_1$-$C_4$ alkyl) group), wherein the halogen atom means fluorine, chlorine, bromine, or iodine atoms, and fluoroalkyl or fluoroalkoxy groups indicate alkyl or alkoxy groups with one or more hydrogen atoms being substituted by fluorine atoms, and further wherein when two or more substituted groups are present, these substituted groups may be either the same or different.

* * * * *